(12) United States Patent
Kataoka et al.

(10) Patent No.: US 9,222,934 B2
(45) Date of Patent: *Dec. 29, 2015

(54) REAGENT AND REAGENT KIT FOR ANALYSIS OF IMMATURE LEUKOCYTE

(71) Applicant: SYSMEX CORPORATION, Kobe-shi (JP)

(72) Inventors: Yukiko Kataoka, Kobe (JP); Tomohiro Tsuji, Kobe (JP); Shinichiro Oguni, Kobe (JP); Ayumu Yoshida, Kobe (JP); Masaki Abe, Hamburg (DE)

(73) Assignee: SYSMEX CORPORATION, Hyogo (JP)

( * ) Notice: Subject to any disclaimer, the term of this patent is extended or adjusted under 35 U.S.C. 154(b) by 0 days.

This patent is subject to a terminal disclaimer.

(21) Appl. No.: 13/956,939

(22) Filed: Aug. 1, 2013

(65) Prior Publication Data

US 2014/0038179 A1    Feb. 6, 2014

Related U.S. Application Data

(63) Continuation of application No. 12/666,770, filed as application No. PCT/JP2008/061573 on Jun. 25, 2008, now Pat. No. 8,859,200.

(30) Foreign Application Priority Data

Jun. 25, 2007   (JP) .................. 2007-166639

(51) Int. Cl.
| | | |
|---|---|---|
| *C12P 21/04* | (2006.01) | |
| *G01N 33/50* | (2006.01) | |
| *G01N 33/569* | (2006.01) | |
| *G01N 15/10* | (2006.01) | |
| *G01N 15/14* | (2006.01) | |

(52) U.S. Cl.
CPC ........ *G01N 33/5094* (2013.01); *G01N 15/1459* (2013.01); *G01N 33/56972* (2013.01); *G01N 2015/1006* (2013.01); *G01N 2015/1402* (2013.01); *Y10S 435/81* (2013.01)

(58) Field of Classification Search
CPC .............. G01N 33/56972; G01N 33/5094; G01N 15/1459; G01N 2015/1006; G01N 2015/1402
See application file for complete search history.

(56) References Cited

U.S. PATENT DOCUMENTS

| | | | |
|---|---|---|---|
| 5,389,549 A | 2/1995 | Hamaguchi et al. | |
| 5,413,938 A | 5/1995 | Tsujino et al. | |
| 5,958,776 A | 9/1999 | Sakata et al. | |
| 6,664,110 B1 | 12/2003 | Tsuji et al. | |
| 6,869,798 B2 | 3/2005 | Crews et al. | |
| 2002/0086344 A1 | 7/2002 | Tsuji et al. | |
| 2003/0219850 A1 | 11/2003 | Tsuji et al. | |
| 2005/0202400 A1 | 9/2005 | Tsuji et al. | |
| 2007/0178597 A1* | 8/2007 | Tsuji et al. ........ | 436/63 |
| 2007/0231913 A1* | 10/2007 | Tsuji et al. ........ | 436/63 |

FOREIGN PATENT DOCUMENTS

| | | |
|---|---|---|
| EP | 0444240 A1 | 4/1991 |
| EP | 0525398 A2 | 2/1993 |
| EP | 1 004 880 A2 | 5/2000 |
| JP | 03-252556 A | 11/1991 |
| JP | 05-099919 A | 4/1993 |
| JP | 06-273413 A | 9/1994 |
| JP | 10-206423 A | 8/1998 |
| JP | 2000-162209 A | 6/2000 |
| JP | 2002-207036 A | 7/2002 |
| JP | 2002-223791 A | 8/2002 |
| JP | 2003-329668 A | 11/2003 |
| JP | 2003329668 A * | 11/2003 |
| JP | 2006-091024 A | 4/2006 |
| JP | 2006-208401 A | 8/2006 |
| WO | 01/86264 A1 | 11/2001 |
| WO | 2004/001408 A1 | 12/2003 |

OTHER PUBLICATIONS

Machine translation of JP 2003-329668 downloaded from the JPO Jul. 30, 2015.*
Zhou et al, Environmental Pollution (2011) 159: 1198-1204.

* cited by examiner

*Primary Examiner* — Susan Hanley
(74) *Attorney, Agent, or Firm* — Sughrue Mion, PLLC

(57) ABSTRACT

The present invention provides a reagent for analysis of immature leukocytes comprising:
  a surfactant which can damage cell membranes of erythrocytes and mature leukocytes,
  a solubilizing agent which can shrink the damaged blood cells and
  at least one dye for staining nucleic acid selected from the dyes of the formulae (I) and (II), wherein $X^-$ is an anion.

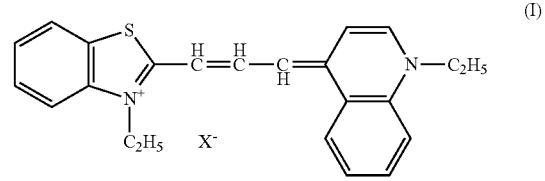

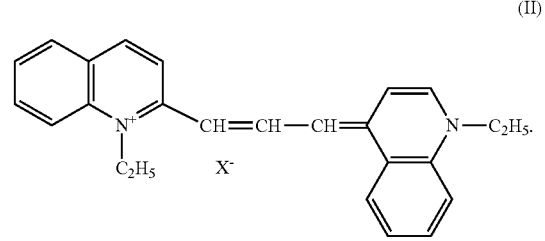

18 Claims, 12 Drawing Sheets

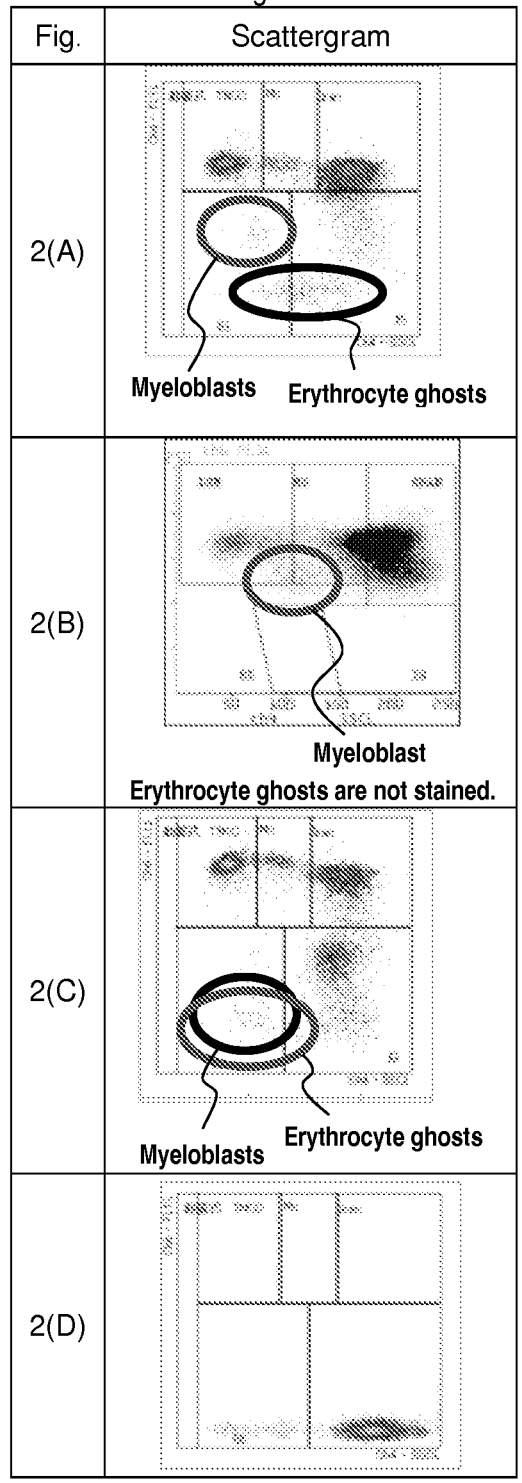

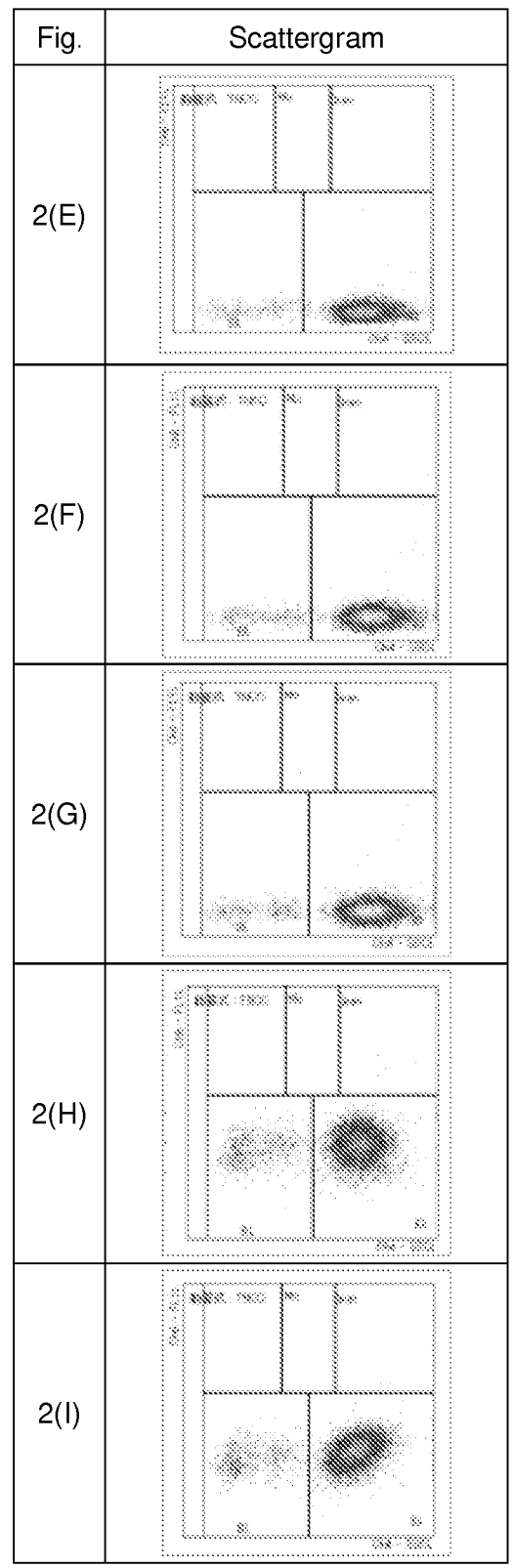

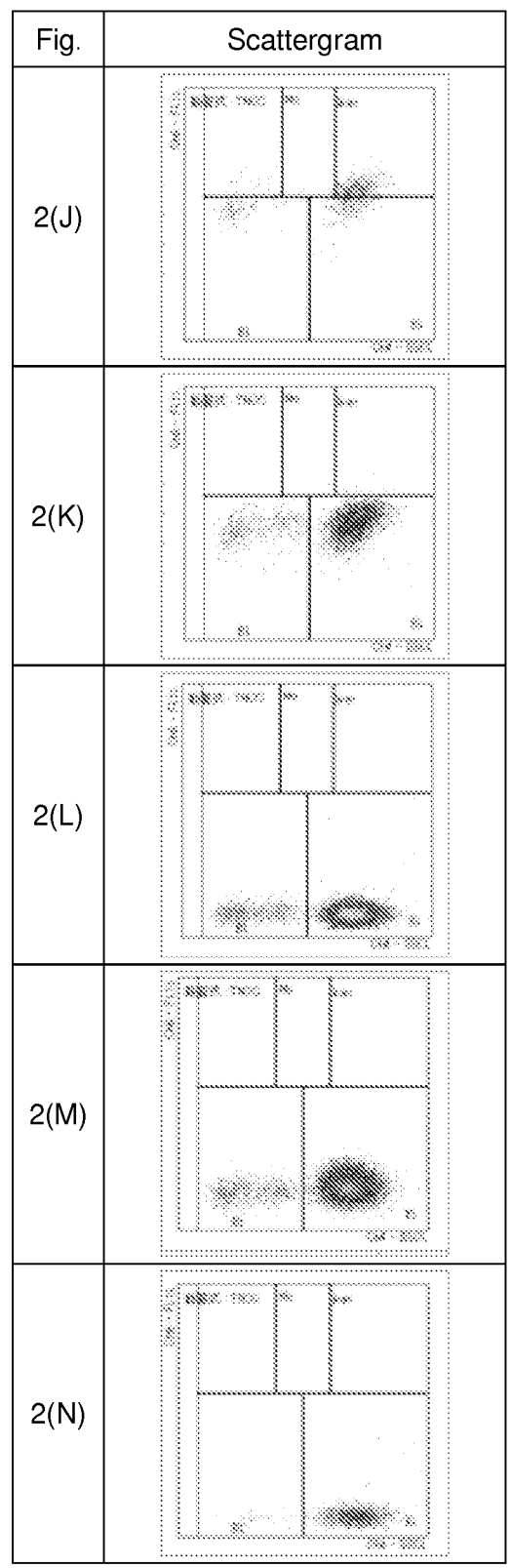

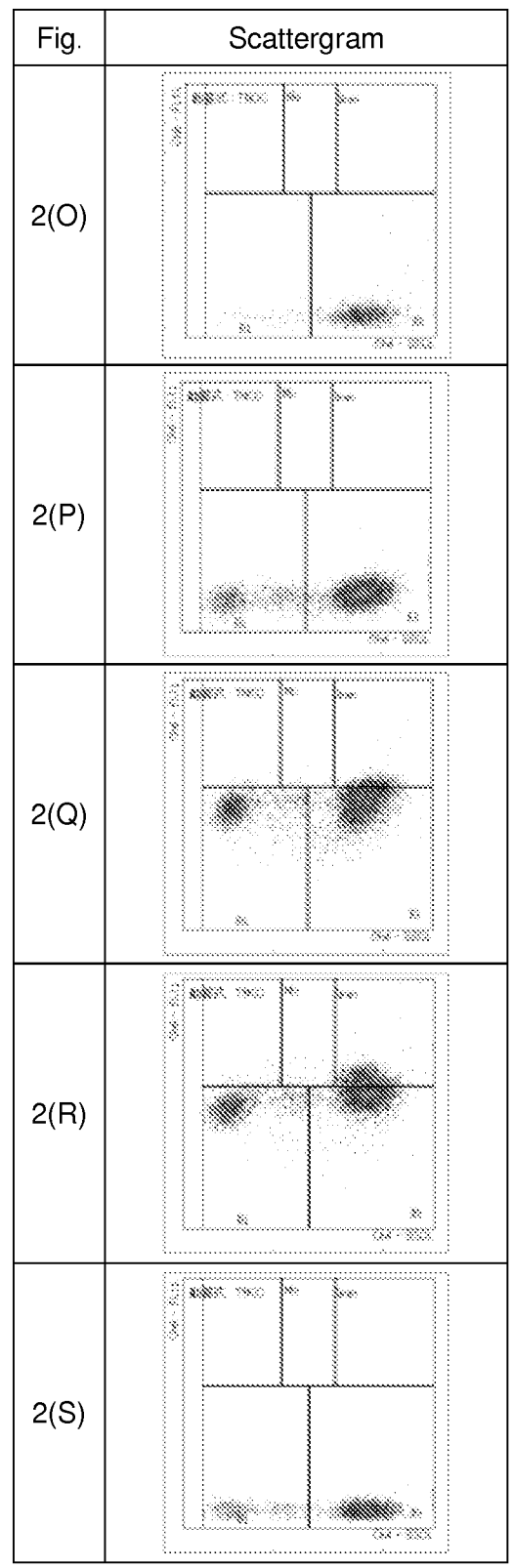

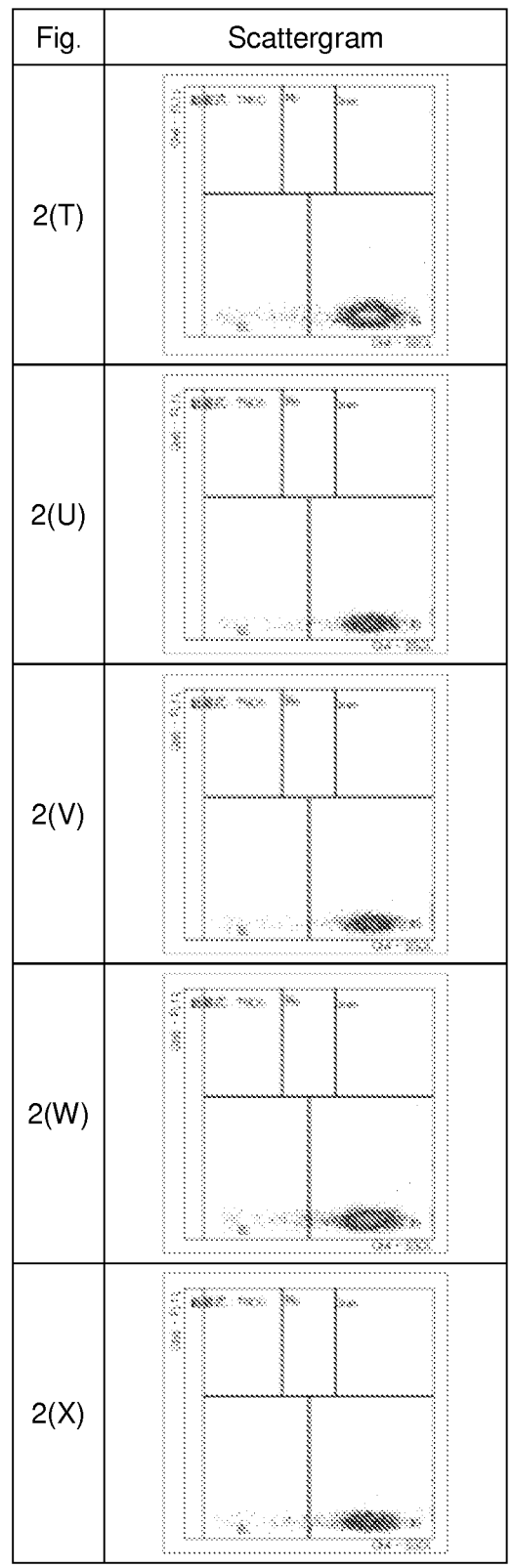

Scattergram

REAGENT AND REAGENT KIT FOR ANALYSIS OF IMMATURE LEUKOCYTE

CROSS REFERENCE TO RELATED APPLICATIONS

This application is a Continuation Application of U.S. patent application Ser. No. 12/666,770 filed Dec. 24, 2009, which is a U.S. National Stage Application of PCT/JP2008/061573 filed Jun. 28, 2008, which claims benefit of Japanese Application 2007-166639 filed Jun. 25, 2007. The above-noted applications are incorporated herein by reference in their entirety.

TECHNICAL FIELD

The present invention relates to a reagent and reagent kit for classifying and counting leukocytes in a biological sample.

BACKGROUND ART

Blood cells are produced in bone marrow, differentiated from immature cells to mature cells and migrated into peripheral blood. In healthy subject, immature leukocytes do not appear in peripheral blood. However, in some cases, immature leukocytes appear in peripheral blood of patients suffering from leukemia, cancer metastasis to the bone marrow, multiple myeloma, severe infection or the like. Therefore, it is very important to classify and measure mature and immature leukocytes in biological samples in order to diagnose these diseases.

A reagent disclosed in Japanese Unexamined Patent Publication No. Hei 10(1998)-206423 is known as a reagent for measuring immature leukocytes. This reagent is mixed with a biological sample to form a measurement sample, the obtained measurement sample is introduced into a flow cytometer and mature and immature leukocytes in the sample are classified and respectively counted based on optical information obtained by applying light having a specific wave length. Further, immature leukocytes can be further classified into myeloblasts, immature granulocytes and the like and they can be measured respectively.

DISCLOSURE OF THE INVENTION

Problems that the Invention is to Solve

However, in analysis of blood cells using the conventional reagent, the signal region of myeloblasts among immature leukocytes to be classified partially overlaps with the signal region of the debris of lysed erythrocytes (erythrocyte ghosts), in some cases. As a result, the myeloblasts and the debris of erythrocytes are detected in the overlapped region in scattergrams, thereby higher amount of myeloblasts being detected than its actual amount. For example, peripheral blood from patients suffering from the specific diseases such as multiple myeloma, bile duct cancer, peritonitis, diabetes, gromerular nephritis, pleurisy or the like does not contain myeloblasts. However, when blood samples taken from such patients are analyzed using the conventional reagent, accurate blood cell analyses could not be carried out because the signal of the debris of erythrocytes was incorrectly recognized as the signal of myeloblasts. The reason for this is considered to be that erythrocytes in the sample from such specific patients are not lysed properly, different from erythrocytes in the sample from healthy subject or patients with diseases other than those described above. There is a possibility of false diagnoses and treatments if the amount of myeloblasts detected in peripheral blood is higher than their actual amount. As used herein, the term "erythrocyte ghost" means erythrocytes which lost their hemoglobin as a result of the reaction of a blood sample and a regent for blood analysis, but did not shrink sufficiently.

Therefore, the purpose of the present invention is to provide a reagent which makes it possible to classify and count immature leukocytes more precisely even when blood samples taken from the patients with such specific diseases as described above are analyzed.

Means for Solving the Problems

The present inventors have made intensive studies to solve the above-described problems and found that the above problems can be solved by using a reagent comprising at least one dye for staining nucleic acid selected from a dye of the following formula (I):

$$\text{(I)}$$

wherein $X^-$ is an anion; and
a dye of the following formula (II):

$$\text{(II)}$$

wherein $X^-$ is an anion.

Therefore, one aspect of the present invention is a reagent for analysis of immature leukocytes comprising:
a surfactant which can damage cell membranes of erythrocytes and mature leukocytes,
a solubilizing agent which can shrink the damaged blood cells and
at least one dye for staining nucleic acid selected from the dyes of the above formulae (I) and (II).

Another aspect of the present invention is a reagent kit for analysis of immature leukocytes comprising:
a first reagent which comprises a surfactant that can damage cell membranes of erythrocytes and mature leukocytes and a solubilizing agent that can shrink the damaged blood cells, and
a second reagent which comprises at least one dye for staining nucleic acid selected from the dyes of the above formulae (I) and (II).

Effect of the Invention

The reagent and reagent kit for analysis of immature leukocytes of the present invention allow more precise classification and counting of immature leukocytes and mature leukocytes compared to the conventional reagent, even when biological samples from patients suffering from the specific diseases such as multiple myeloma, bile duct cancer, peritonitis, diabetes, gromerular nephritis, pleurisy or the like are analyzed.

DESCRIPTION OF THE REFERENCE NUMERALS

Figure 1:
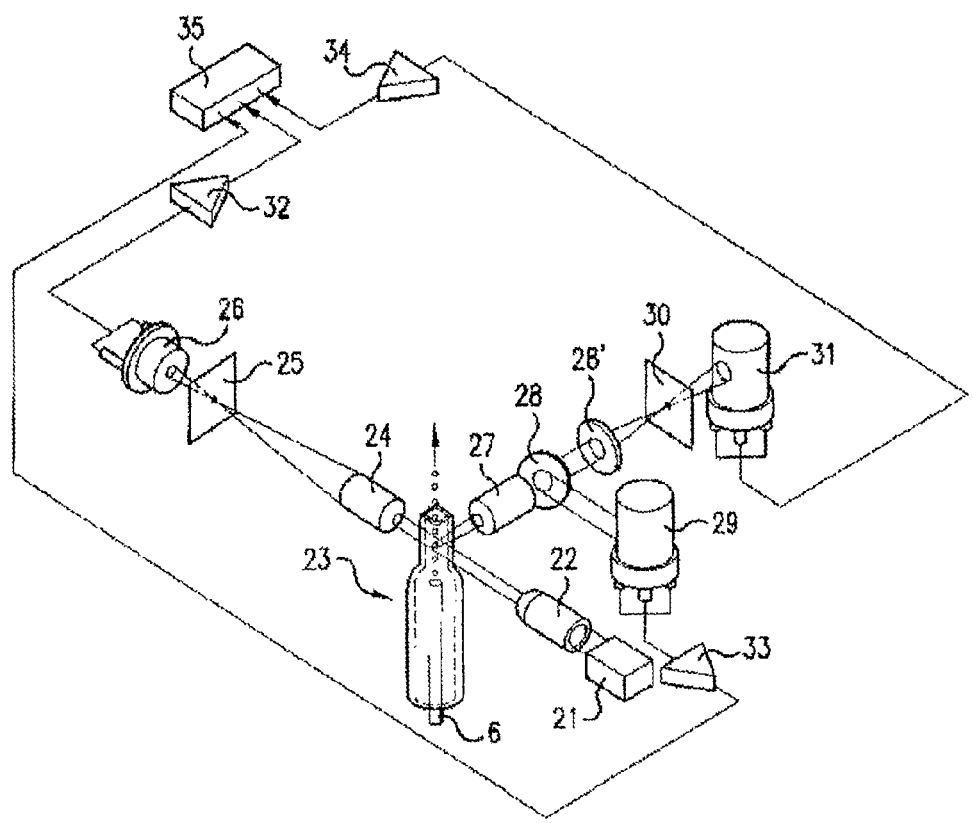
FIG. 1 is a schematic representation showing an example of a flow cytometer which can be used for analyses of immature leukocytes using the reagent or reagent kit of the present invention.

6 Nozzle
21 Light source
22 Collimator lens
23 Flow cell
24 Condensing lens
25 Pin hole plate
26 Forward scattered light detector
27 Condensing lens
28 Dichroic mirror
28' Filter
29 Side scattered light detector
30 Pin hole plate
31 Side fluorescence detector
32, 33 and 34 Amplifiers
35 Analyzing part

BEST MODE FOR CARRYING OUT THE INVENTION

The reagent for analysis of immature leukocytes of the present embodiment (hereinafter referred to as "the reagent") makes it possible to classify leukocytes contained in a biological sample into mature and immature leukocytes and to count them respectively. It also makes it possible to classify the mature leukocytes into at least two species such as lymphocytes, monocytes, granulocytes and the like and to count them respectively. Further, the present reagent makes it possible to further classify immature leukocytes into immature granulocytes and myeloblasts and to accurately count them respectively.

The term "immature leukocytes" as used herein refers to immature leukocytes which exist usually in bone marrow and do not occur in peripheral blood of healthy subject. Immature leukocytes include, for example, myeloblasts, promyelocytes, myelocytes, metamyelocytes, and the like. In some cases, promyelocytes, myelocytes and metamyelocytes are collectively called as "immature granulocytes". Myeloblasts include leukocytic hematopoietic precursor cells such as myeloid series stem cells (CFU-GEMN), neutrophil-macrophage colony-forming cells (CFU-GM), eosinophil colony-forming cells (CFU-EOS) and the like.

The biological sample to be analyzed with the reagent of the present embodiment is not limited as long as it comprises leukocytes and includes, for example, blood, urea, bone marrow aspirate, a sample taken in apheresis and the like.

The reagent of the present embodiment comprises the surfactant which can damage cell membranes of erythrocytes and mature leukocytes, the solubilizing agent which can shrink the damaged blood cells and the dye for staining nucleic acid selected from the dyes of the above formulae (I) and (II).

By mixing the biological sample and the reagent, cell membranes of blood cells contained in the sample are damaged by the action of the surfactant. The surfactant tends to damage cell membranes of erythrocytes and mature leukocytes, while cell membranes of immature leukocytes are substantially resistant to be damaged. The damaged blood cells such as erythrocytes and mature leukocytes shrink by the action of the solubilizing agent. On the other hand, because cell membranes of immature leukocytes are difficult to be damaged, these cells are less shrunk by the solubilizing agent than erythrocytes and mature leukocytes. Among the damaged blood cells, the nuclei of leukocytes tend to be stained intensely by the action of the dye for staining nucleic acid. However, the undamaged immature leukocytes are difficult to be stained. In addition, because erythrocytes do not have nuclei, they are difficult to be stained by the above dye for staining nucleic acid. As a consequence, immature leukocytes, mature leukocytes and erythrocytes can be respectively discriminated.

Now, it has been found that by using at least one dye for staining nucleic acid selected from the dyes having the above formulae (I) and (II), the debris of erythrocytes are clearly distinguished from the blood cells to be measured even in the biological samples from patients suffering from the specific diseases such as multiple myeloma, bile duct cancer, peritonitis, diabetes, gromerular nephritis, pleurisy or the like. It has also been found that the myeloblasts can be more clearly discriminated from the debris of erythrocytes even when the blood samples containing myeloblasts are used. Further, the present reagent makes it possible to distinguish immature leukocytes from mature leukocytes as clearly as the conventional reagent does even in the biological samples from the patients suffering from the diseases other than the specific diseases described above.

In the formulae (I) and (II) of the dye for staining nucleic acid, the anion of $X^-$ may include halogen ions (fluoride, chloride, bromide or iodide ion), boron halide ions ($BF_4^-$, $BCl_4^-$, $BBr_4^-$, etc.), phosphorus compound ions, halogeno-oxygen acid ions, fluorosulfuric acid ions, methyl sulfate ions, and tetraphenyl boron compound ions which have a halogen or halogeno-alkyl group as a substituent on the aromatic rings. Among them, iodide ion is preferred.

The concentration of the above dye in the reagent is preferably 0.01 to 500 ppm, and more preferably 0.1 to 200 ppm.

It is preferred to use at least two surfactants which can damage cell membranes of erythrocytes and mature leukocytes. More preferably, two surfactants are used. By using two or more surfactants, immature leukocytes can be more clearly discriminated from mature leukocytes.

It is preferable that at least one of the above surfactants is an nonionic surfactant. More preferably, all surfactants to be used are nonionic surfactants. The nonionic surfactant is preferably a polyoxyethylene nonionic surfactant, and more preferably, the polyoxyethylene nonionic surfactant having the following formula (III):

  (III)

(wherein $R^1$ represents a $C_{9-25}$ alkyl, alkenyl or alkynyl group; $R^2$ represents —O—, —COO— or

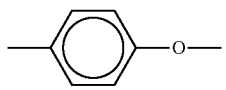

and n is an integer of 10 to 40).

The surfactant represented by the above formula (III) may include polyoxyethylene(15)oleyl ether, polyoxyethylene(20)oleyl ether, polyoxyethylene(20)stearyl ether, polyoxyethylene(15)cetyl ether, polyoxyethylene(20)cetyl ether and the like.

The surfactant to be used in the reagent of the present embodiment is preferably polyoxyethylene oleyl ether and polyoxyethylene stearyl ether, and specifically preferably, at least one of the surfactants is polyoxyethylene oleyl ether. More preferably, the polyoxyethylene oleyl ether and polyoxyethylene stearyl ether have the formula (III) wherein n is 15 to 20. Still more preferably, the polyoxyethylene oleyl ether is polyoxyethylene(15)oleyl ether or polyoxyethylene(20)oleyl ether. The exemplary combination of the surfactants can include the combination of polyoxyethylene(15)oleyl ether and polyoxyethylene(20)oleyl ether, or the combination of polyoxyethylene(15)oleyl ether and polyoxyethylene(20)stearyl ether.

The concentration of the surfactant in the reagent can be appropriately selected according to the type of the surfactant. The concentration of one or more surfactants in total in the reagent is 500 to 50,000 ppm, more preferably 3,500 to 35,000 ppm. When at least one of the surfactants is polyoxyethylene oleyl ether, the concentration of one or more surfactants in total in the reagent is preferably 500 to 50,000 ppm, more preferably 3,500 to 35,000 ppm.

When polyoxyethylene(15)oleyl ether and polyoxyethylene(20)oleyl ether are used as the surfactants, the concentration of these in total in the reagent is preferably 500 to 50,000 ppm, more preferably 3,500 to 35,000 ppm.

When multiple surfactants are used, the mixing ratio of these surfactants can be appropriately selected according to a hydroxyl value of the surfactants. For example, when polyoxyethylene(15)oleyl ether having the hydroxyl value of 64.8 and polyoxyethylene(20)oleyl ether having the hydroxyl value of 52.4 are used, the mixing ratio is preferably 1:1.

When multiple surfactants are used and at least one of them is polyoxyethylene oleyl ether, it is preferable that the amount of the polyoxyethylene oleyl ether preferably accounts for more than 50% of the sum of the multiple surfactants. Due to this, immature leukocytes are more clearly discriminated from mature leukocytes.

The above solubilizing agent may include, for example, sarcosine derivatives, cholic acid derivatives, methylglucanamides and the like. One or more selected among them can be used.

Sarcosine derivatives include the sarcosine derivatives having the following structural formula and salts thereof. Specifically, sodium N-lauroylsarcosinate, sodium lauroyl methyl β-alanine, lauroylsarcosine and the like are mentioned. Colic acid derivatives include the colic acid derivatives having the following structural formula and salts thereof. Specifically, CHAPS (3-[(3-cholamidopropyl)dimethylammonio]-1-propanesulfonate), CHAPSO ([(3-cholamidopropyl)dimethylammonio]-2-hydroxy-1-propanesulfonate) and the like are mentioned. Methylglucanamides include MEGA8 (octanoyl-N-methylglucamide), MEGA9 (nonanoyl-N-methylglucamide), MEGA10 (decanoyl-N-methylglucamide) and the like.

Sarcosine derivatives have the following structural formula:

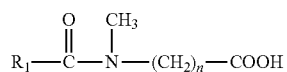

wherein $R_1$ is a $C_{10-22}$ alkyl group; and n is 1 to 5.

Colic acid derivatives have the following structural formula:

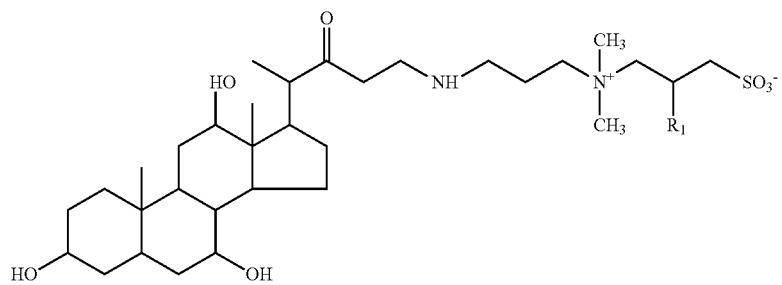

wherein $R_1$ is a hydrogen atom or a hydroxy group.

Methylglucanamides have the following structural formula:

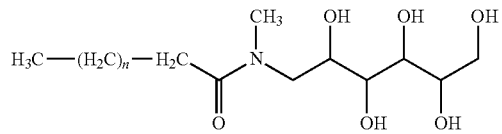

wherein n is 5 to 7.

The concentration of the solubilizing agent in the reagent can appropriately be selected according to the type of the solubilizing agent used. When the sarcosine derivative is used as the solubilizing agent, the concentration of the solubilizing agent in the reagent is preferably 50 to 3,000 ppm. When the colic acid derivative is used, it is preferably 100 to 10,000 ppm. When the methylglucanamide is used, it is preferably 1,000 to 8,000 ppm.

Further, n-octyl β-glucoside, sucrose monocaprate, N-formylmethylleucylalanine and the like can be used as the solubilizing agent. When these are used, the concentration thereof in the reagent is preferably 10 to 50,000 ppm. One or more solubilizing agents may be used alone or in combination.

The osmotic pressure of the reagent is not specifically limited but is preferably 10 to 600 mOsm/kg. The osmotic pressure of the reagent can be appropriately adjusted by adding saccharides, amino acids, sodium chloride and the like. It can also be adjusted by regulating the concentration of a buffering agent.

The saccharides may mention monosaccharides such as glucose, fructose and the like; polysaccharides such as arabinose and the like; and sugar alcohols such as xylitol, sorbitol, mannitol, ribitol and the like, without any limitation thereto. It is preferable that at least one saccharide selected from the group consisting of xylitol, arabinose, glucose, mannitol, sorbitol and ribitol is used as the saccharide.

The concentration of the saccharide in the reagent can appropriately be selected according to the desired osmotic pressure. When xylitol is used, for example, it may be used in an amount of 0 to 75 g/L, more preferably 20 to 50 g/L in the reagent.

The amino acids may include valine, proline, glycine, alanine and the like. It is preferred to use at least one amino acid selected from the group consisting of valine, proline, glycine and alanine, and more preferably, either or both of glycine and alanine are used as the amino acid.

The amount of the amino acid in the reagent can be appropriately selected according to the desired osmotic pressure. When glycine is used, for example, it may be used in an amount of 0 to 50 g/L, more preferably 10 to 30 g/L in the reagent.

The reagent of the present embodiment may contain sodium chloride in order to adjust the osmotic pressure, as described above. However, when the amount of sodium chloride contained in the reagent is high, the longer the reaction time is, or the higher the reaction temperature is, the more myeloblasts among immature leukocytes are damaged and the more nuclei thereof are stained by the dye. If myeloblasts are stained, the fluorescence intensity of the myeloblasts detected is similar to that of mature leukocytes, thereby decreasing the accuracy of the classification between mature leukocytes and myeloblasts. Thus, the concentration of sodium chloride in the reagent is preferably 0.01 to 3 g/L, and more preferably 0 g/L (not contained), in order to avoid any adverse effect on measurements.

The reagent of the present embodiment preferably has pH of 5.0 to 9.0. The pH of the reagent can be adjusted with a buffering agent. The buffering agent used can be, for example, Good buffer such as HEPES, phosphate buffered saline and a pH adjusting agent such as sodium hydroxide.

The reagent of the present embodiment can be obtained by dissolving the above surfactant, solubilizing agent, dye for staining nucleic acid and optional component(s) in an appropriate medium with the concentrations described above. The appropriate medium is not limited as long as it can dissolve the above components and includes water, alcohol, ethylene glycol, dimethylsulfoxide (DMSO), the mixture thereof and the like.

The above surfactant, solubilizing agent and dye for staining nucleic acid can be used as a single reagent to be mixed with a biological sample for analysis of immature leukocytes. Alternatively, a reagent kit containing a first reagent comprising the surfactant and solubilizing agent and a second reagent comprising the dye for staining nucleic acid can be used for analysis of immature leukocytes.

Therefore, the present invention also provides a reagent kit for analysis of immature leukocytes comprising a first reagent which comprises a surfactant that can damage cell membranes of erythrocytes and mature leukocytes and a solubilizing agent that can shrink the damaged blood cells, and a second reagent which comprises at least one dye for staining nucleic acid selected from the dyes of the above formulae (I) and (II).

The concentrations of the surfactant and solubilizing agent in the above first reagent may be such that the concentrations thereof described above for the reagent for analysis of immature leukocytes can be obtained when the first reagent is mixed with the second reagent. The first reagent can be obtained by dissolving the surfactant and solubilizing agent to the appropriate medium described above.

The concentration of the dye for staining nucleic acid in the second reagent may be such that the concentration thereof described above for the reagent for analysis of immature leukocytes can be obtained when the second reagent is mixed with the first reagent. It is preferable that the second reagent is the one in which the dye for staining nucleic acid is dissolved in an organic solvent such as ethylene glycol because the storage stability of the dye can be improved.

The reagent and reagent kit can be used for the analysis of immature leukocytes by preparing a measurement sample by mixing the reagent(s) with a biological sample and subjecting the measurement sample to a flow cytometer. The mixing ratio (by volume) of the biological sample and the reagent or the sum of the first and second reagents in the reagent kit is preferably 1:10 to 1:1,000.

In the reagent kit, the mixing ratio (by volume) of the first and second reagents is preferably 1,000:1 to 10:1.

When the reagent kit is used, the order of addition for mixing the respective reagent in the reagent kit and the biological sample is not specifically limited. Preferably, the first reagent and the second reagent are mixed and then the biological sample is added thereto.

The mixing of the reagent or the reagents in the reagent kit and the biological sample is preferably carried out at a temperature of 20 to 40° C. for 3 to 15 seconds. When the reaction temperature is high, the reaction time can be shorter; when the reaction temperature is low, the reaction time can be longer.

When a flow cytometer is used for the analysis, light can be applied to the blood cells in the measurement sample flowing through a flow cell to obtain optical information such as scattered light, fluorescence and the like. The species and number of the blood cells can be measured based on the information.

Specifically, the above analysis can be carried out by using the flow cytometer shown in FIG. 1. In the following, a measurement of myeloblasts is described as an example of the present embodiments.

A measurement sample discharged from a nozzle 6 flows through an orifice portion of a flow cell 23. Blood cells in the sample pass through the orifice portion in a line. Light emitted from a light source 21 is applied via a collimator lens 22 to blood cells flowing through the flow cell 23. Side scattered light, side fluorescence and forward scattered light are generated by applying light to the blood cells. The side scattered light is introduced into a side scattered light detector (photomultiplier tube) 29 through a condensing lens 27 and a dichroic mirror 28. The side fluorescence is introduced into a side fluorescence detector (photomultiplier tube) 31 through the condensing lens 27, the dichroic mirror 28, a filter 28' and a pin hole plate 30. The forward scattered light is introduced into a forward scattered light detector (photodiode) 26 through a condensing lens 24 and a pin hole plate 25.

The forward scattered light signal, side scattered light signal and side fluorescence signal generated from the forward scattered light detector 26, the side scattered light detector 29 and the side fluorescence detector 31, respectively, are amplified by amplifiers 32, 33, and 34, respectively, and introduced into an analyzing part 35.

The analyzing part 35 calculates the intensities of the forward scattered light, side scattered light and fluorescence respectively from the introduced forward scattered light signal, side scattered light signal and side fluorescence signal. The analyzing part 35 generates a first two-dimensional distribution map having two axes of the forward scattered light intensity and the fluorescence intensity and identifies a region where all leukocytes in the sample appear (total leukocyte region) on the two-dimensional distribution map. Further, the analyzing part generates a second two-dimensional distribution map having two axes of the side scattered light intensity and the fluorescence intensity of the cells appearing in the total leukocyte region. On this two-dimensional distribution map, a region where mature leukocytes appear (mature leukocyte region), a region where lymphocytes appear (lymphocyte region), a region where monocytes appear (monocyte region) and a region where granulocytes appear (granulocyte region) are established. Further, a region where myeloblasts appear (myeloblast region 1) and a region where immature granulocytes appear (immature granulocyte region) are identified.

Then, a third two-dimensional distribution map is generated having two axes of the side scattered light intensity and the forward scattered light intensity, and a region where myeloblasts appear (myeloblast region 2) on this two-dimensional distribution map is identified. The number of myeloblasts contained in the sample is calculated as the number of cells appearing in the myeloblast region 1 and the myeloblast region 2, and the number of immature granulocytes contained in the sample is calculated as the number of cells appearing in the immature granulocyte region. Incidentally, because myeloblasts have large size and have single nucleus, they generate strong forward scattered light intensity and weak side scattered light intensity. In addition, they generate weak fluorescence intensity because they are hardly stained, as described above. Because immature granulocytes have large size and their nuclei are segmented, they generate strong forward scattered light intensity and side scattered light intensity. In addition, they generate weak fluorescence intensity because they are hardly stained.

EXAMPLES

The present invention will be explained by the following examples in more detail. However, the present invention is not limited by the following examples.

Example 1

A first reagent and second reagent having the following composition were prepared.
<First Reagent>

| | |
|---|---|
| Polyoxyethylene(15)oleyl ether (Nikko Chemicals) | 12,500 ppm |
| Polyoxyethylene(20)oleyl ether (Nikko Chemicals) | 12,500 ppm |

-continued

| | |
|---|---|
| Sodium N-lauroylsarcosinate (commercial product) | 750 ppm |
| Xylitol (commercial product) | 35.5 g/L |
| HEPES (commercial product) | 30 mM |
| Purified water | 1 L |

The above components were mixed and pH was adjusted to 7.0 with NaOH. The osmotic pressure and electric conductivity of the first reagent were 300 mOsm/kg and 0.59 mS/cm, respectively.
<Second Reagent>

| | |
|---|---|
| Dye for staining nucleic acid | 50 ppm |
| Ethylene glycol | 1 L |

The dye was dissolved into ethylene glycol to prepare the second reagent. As the dye for staining nucleic acid, the dye represented in Table 1 (NK-321) was used.

The first reagent (980 µL), 20 µL of the second reagent and 20 µl of a blood sample containing no myeloblasts taken from a patient with multiple myeloma were mixed and reacted at 35° C. for 7 seconds to prepare a measurement sample. The obtained measurement sample was subjected to the flow cytometer shown in FIG. 1 and side scattered light intensity, forward scattered light intensity and fluorescence intensity were measured. The light source used was red semiconductor laser.

Based on the obtained forward scattered light intensity and fluorescence intensity, a first two-dimensional distribution map having two axes of the forward scattered light intensity and the fluorescence intensity was generated (not shown). According to this first two-dimensional distribution map, the total leukocyte region was identified (not shown). The number of the cells appearing in the identified total leukocyte region was calculated as the number of total leukocytes contained in the sample. For the cells appearing in the identified total leukocyte region, a second two-dimensional distribution map (scattergram) having two axes of the side scattered light intensity and fluorescence intensity was generated. On this scattergram, the myeloblast region can be identified as a region which has low side scattered light intensity and low fluorescence intensity. The obtained scattergram is shown in FIG. 2A (see also Table 1). In the scattergrams of FIG. 2, the x-axis of the scattergram represents side scattered light intensity and the y-axis represents the fluorescence intensity. In the scattergram, "Ly", "Mo", "Gran", "BL" and "IG" represent the sections in which lymphocytes, monocytes, granulocytes, myeloblasts and immature granulocytes appear, respectively. In the present Example 1, almost no signal was detected in the myeloblast region on the scattergram.

Example 2

The analysis was carried out as described in Example 1, except that the dye for staining nucleic acid in the second region was changed to the dye described in Table 1.

The obtained scattergram is shown in FIG. 2(B).

TABLE 1

| Ex. | Dye | Scattergram |
|---|---|---|
| 1 | [benzothiazole-CH=CH-CH= quinoline structure with N+-C2H5 and N-C2H5, I- counterion] | FIG. 2(A) |
| 2 | [quinoline-CH=CH-CH= quinoline structure with N+-C2H5 and N-C2H5, I- counterion] | FIG. 2(B) |

Comparative Examples 1 to 23

The analyses were carried out as described in Example 1, except that the dye in the second reagent was changed to the dye described in

TABLE 2

Figure 2Y:
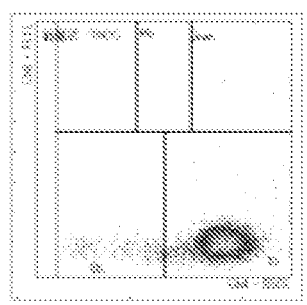
FIG. 2 includes scattergrams of Examples 1 and 2 and Comparative Examples 1 to 23 in FIGS. 2(A)-2(Y).

The obtained scattergrams are shown in FIGS. 2C-2Y.

| Comp. Ex. | Dye | Scattergram |
|---|---|---|
| 1 | [benzothiazole (N+-CH3) -CH=CH-CH= quinoline-N-CH2CH2OH, $BF_4^-$] | FIG. 2(C) |
| 2 | [triphenylmethane dye: phenyl-C(=C6H4-N(CH3)2)(C6H4-N+(CH3)2)Cl-] | FIG. 2(D) |
| 3 | [$C_2H_5$-N+-quinoline-CH=CH-C6H4-N(CH3)2, I-] | FIG. 2(E) |
| 4 | [$C_2H_5$-N+-quinoline-CH=CH-CH=CH-C6H4-N(CH3)2, I-] | FIG. 2(F) |
| 5 | [$C_2H_5$-N+-quinoline-(CH=CH)2-C6H4-N(CH3)2, $ClO_4^-$] | FIG. 2(G) |
| 6 | [bis-azo triazole dye: (C2H5)2N-C6H4-N=N-(1,2,4-triazole with N-CH3 groups)-N=N-C6H4-N(C2H5)2] | FIG. 2(H) |

TABLE 2-continued
The obtained scattergrams are shown in FIGS. 2C-2Y.
| Comp. Ex. | Dye | Scattergram |
|---|---|---|
| 7 | 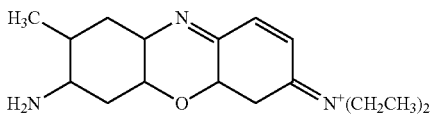 Cl⁻ 1/2 ZnCl₂ | FIG. 2(I) |
| 8 | 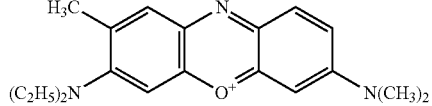 Cl⁻ | FIG. 2(J) |
| 9 | 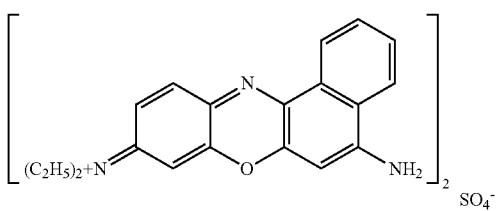 SO₄⁻ | FIG. 2(K) |
| 10 | 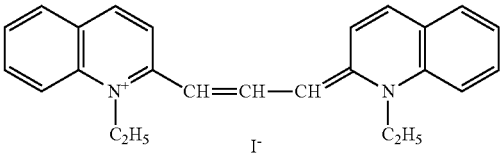 [SMILES: CCN1/C(=C/C=Cc2ccc3ccccc3[n+]2CC)C=Cc2ccccc21 ; [I-]] I⁻ | FIG. 2(L) |
| 11 | 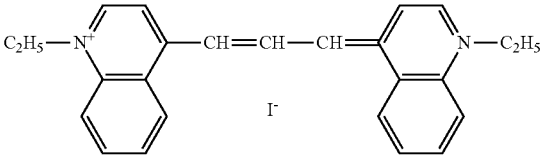 I⁻ | FIG. 2(M) |
| 12 | 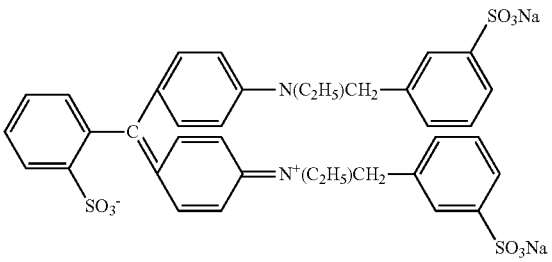 | FIG. 2(N) |
| 13 | 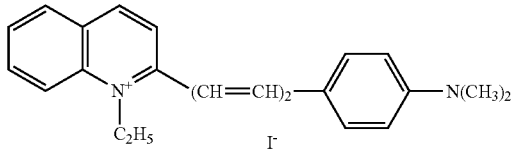 I⁻ | FIG. 2(O) |
| 14 | 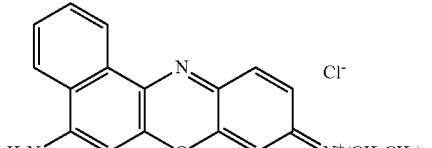 | FIG. 2(P) |

TABLE 2-continued

The obtained scattergrams are shown in FIGS. 2C-2Y.

| Comp. Ex. | Dye | Scattergram |
|---|---|---|
| 15 | Structure with $C_2H_5HN$, $N^+HC_2H_5$, $H_3C$, $ClO_4^-$ (phenoxazine/naphthalene fused system) | FIG. 2(Q) |
| 16 | Benzoselenazole dye: two benzoselenazole units linked by $-(CH=CH)_2-CH=$, N-ethyl, $I^-$ | FIG. 2(R) |
| 17 | Benzoxazole dye: two benzoxazole units linked by $-(CH=CH)_3-CH=$, N-methyl, $I^-$ | FIG. 2(S) |
| 18 | Benzoxazole-quinoline dye linked by $-CH=CH-C(H)=$, N-ethyl, $I^-$ | FIG. 2(T) |
| 19 | Quinolinium-$CH=CH$-phenyl-$N(CH_3)_2$, N-ethyl, $I^-$ | FIG. 2(U) |
| 20 | Bis-quinoline linked by $-CH=$, N-ethyl on both, $I^-$ | FIG. 2(V) |
| 21 | Indoline-benzothiazole linked by $-CH=CH-CH=$, N-ethyl, $I^-$ | FIG. 2(W) |
| 22 | Bis-benzothiazole linked by $-CH=CH-CH=$, with $(CH_2)_3SO_3^-$ and $(CH_2)_3SO_3HN(C_2H_5)_3$ | FIG. 2(X) |
| 23 | Bis-quinoline linked by $-(CH=CH)_2-CH=$, N-ethyl on both, $I^-$ | FIG. 2(Y) |

As can be seen from the results in Table 2, it is possible that by using the reagent for analysis of immature leukocytes comprising the above specific dye, myeloblasts and debris of lysed erythrocytes (erythrocyte ghosts) can be classified and counted even in the blood taken from the patient with multiple myeloma. On the other hand, by using the reagents of Comparative Examples, the signal of myeloblasts and the signal of erythrocyte ghosts or other cells overlapped and clear discrimination was not possible.

Example 3

The first reagent described in Example 1 and the second reagent described in Example 1 whose concentration of the dye for staining nucleic acid is 100 ppm were prepared.

The first reagent (980 μL), 20 μL of the second reagent and 20 μl of any of the following blood samples were mixed and reacted at 35° C. for 7 seconds to prepare measurement samples. Scattergrams were obtained as described in Example 1.

As the blood sample, a blood sample from a leukemia patient containing myeloblasts (hereinafter referred to as "myeloblast sample") or a blood sample from a multiple myeloma patient containing no myeloblast (erythrocytes were lysed improperly) (hereinafter referred to as "improper hemolysis sample") was used.

Based the obtained scattergram, the ratio of myeloblasts to total leukocytes (ratio of myeloblasts=the number of myeloblasts/the number of total leukocytes×100) was calculated according to the following procedures.

Based on the forward scattered light intensity and fluorescence intensity in the measurement sample, a first two-dimensional distribution map (scattergram) having two axes of the forward scattered light intensity and the fluorescence intensity was generated. According to this first scattergram, the total leukocyte region was identified. The number of the cells appearing in the identified total leukocyte region was calculated as the number of total leukocytes contained in the sample. For the cells appearing in the total leukocyte region, a second scattergram having two axes of the side scattered light intensity and fluorescence intensity and a third scattergram having two axes of the side scattered light intensity and the forward scattered light intensity were generated. On the second and third scattergrams, the myeloblast regions 1 and 2 were established, respectively. The number of the cells appearing in the established myeloblast regions 1 and 2 was counted as the number of myeloblasts contained in the sample.

The ratio of myeloblasts to total leukocytes (ratio of myeloblasts=the number of myeloblasts/the number of total leukocytes×100) was calculated.

Figure 3:
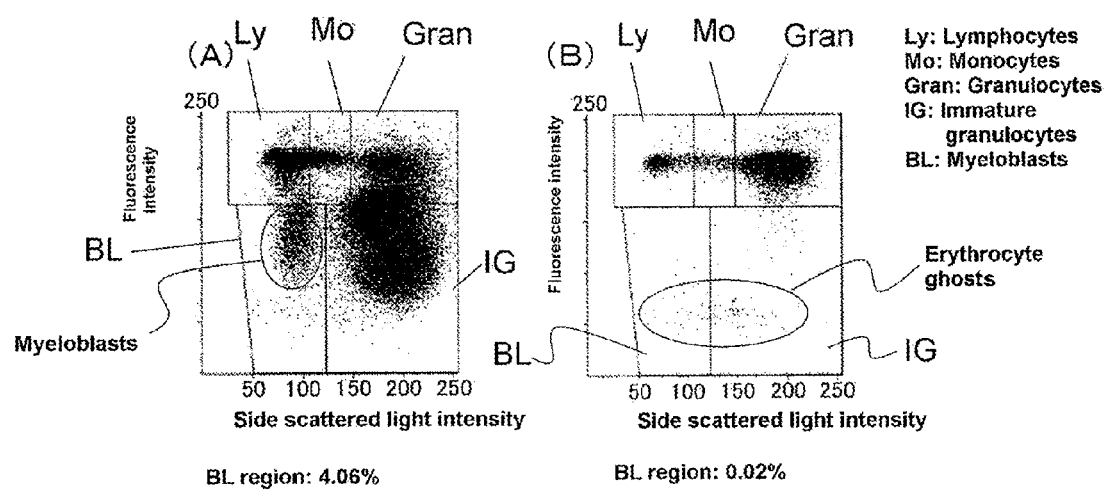
FIGS. 3A and 3B represent scattergrams obtained in Example 3.

FIG. 3 shows the obtained scattergrams and the ratio of myeloblasts to total leukocytes (referred to as "BL region"). In FIG. 3, (A) and (B) represent the results of the myeloblast sample and the improper hemolysis sample, respectively.

According to these results, it is found that by using the reagent of the present invention, the myeloblast region and the erythrocyte ghost region did not overlap on scattergrams in the results for the myeloblast sample and the improper hemolysis sample. Further, myeloblasts were detected in the myeloblast sample and the ratio of myeloblasts is very low in the improper hemolysis sample. Namely, by using the reagent of the present invention, myeloblasts can be clearly distinguished from erythrocyte ghosts and immature leukocytes can be measured accurately because erythrocyte ghosts do not appear in the myeloblast region on the scattergrams even when blood from the patient having multiple myeloma was used.

Examples 4 to 7

A first reagent and second reagent having the composition described in Table 3 below were prepared.

[Table 3]

TABLE 3

Figure 4:
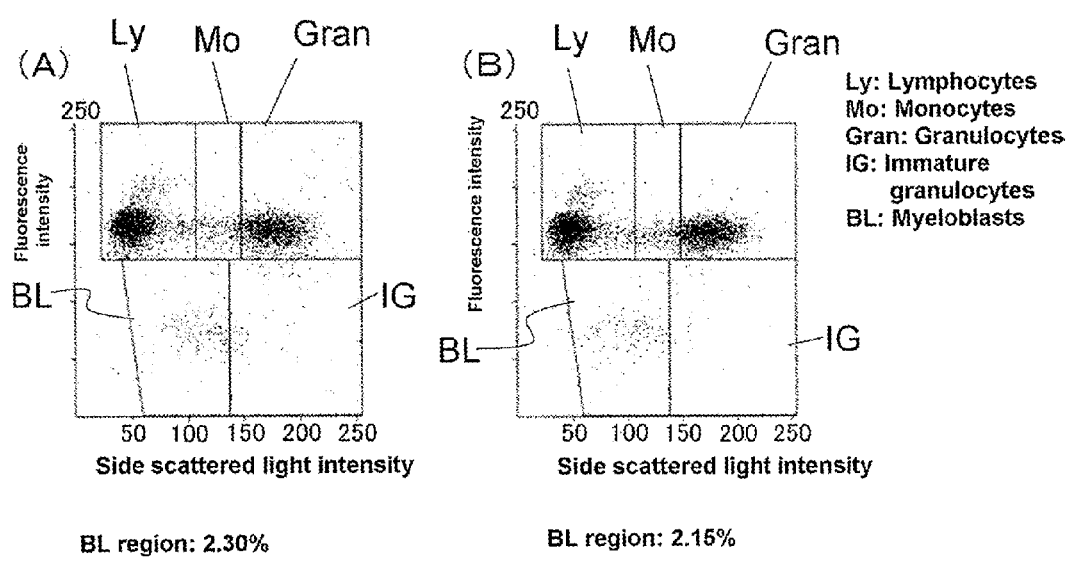
FIGS. 4A and 4B represent scattergrams obtained in Example 4.
Figure 5:
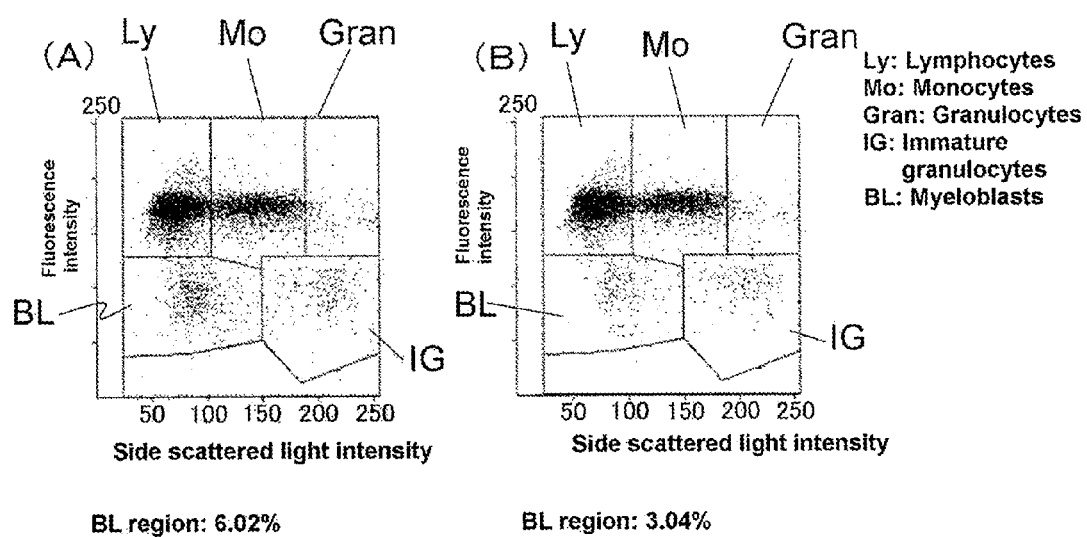
FIGS. 5A and 5B represent scattergrams obtained in Example 5.
Figure 6:
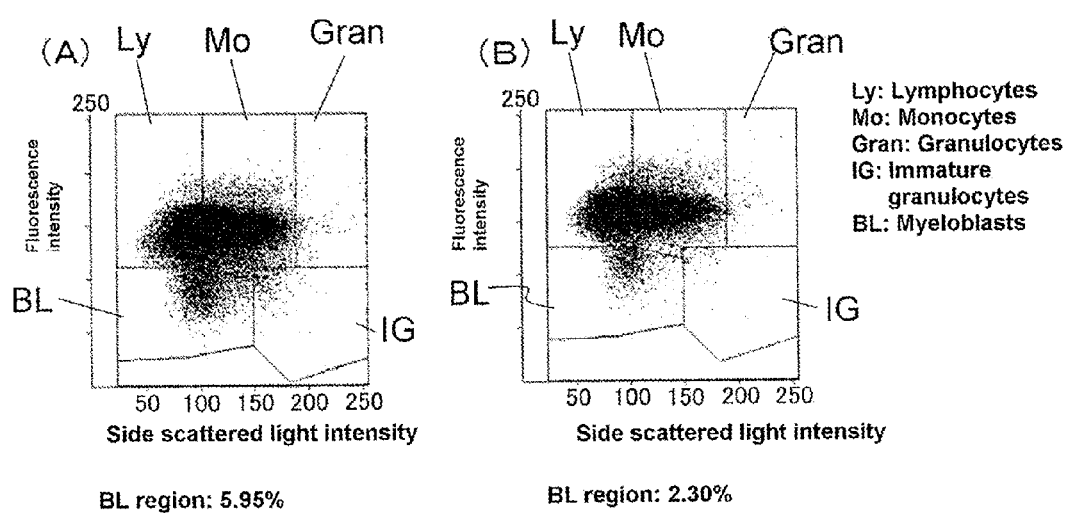
FIGS. 6A and 6B represent scattergrams obtained in Example 6.
Figure 7:
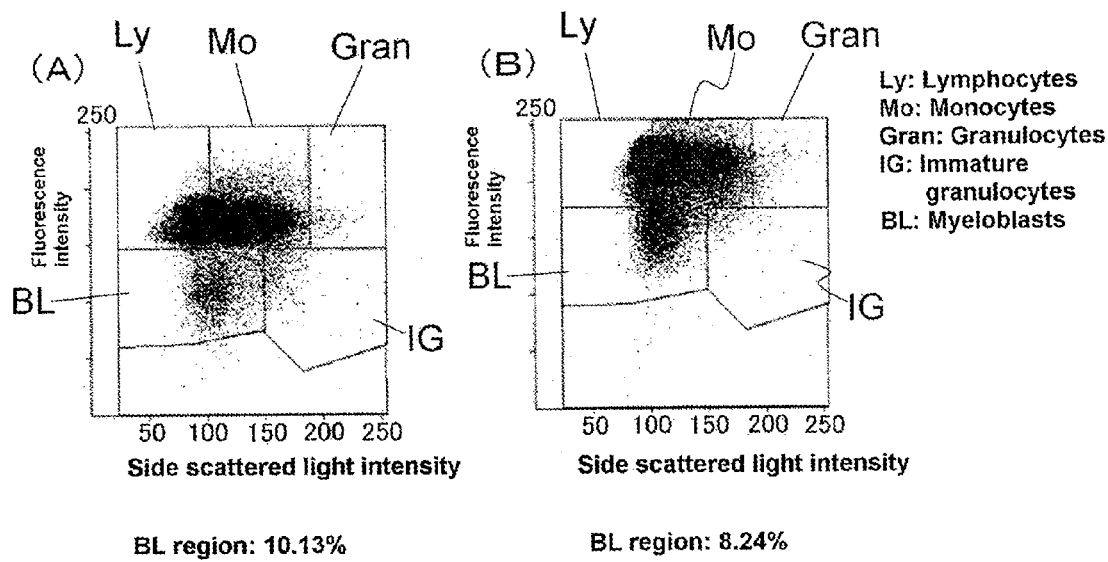
FIGS. 7A and 7B represent scattergrams obtained in Example 7.

| | | Examples (Figs.) | | | | | | | |
|---|---|---|---|---|---|---|---|---|---|
| | | 4A (FIG. 3A) | 4B (FIG. 3B) | 5A (FIG. 4A) | 5B (FIG. 4B) | 6A (FIG. 5A) | 6B (FIG. 5B) | 7A (FIG. 6A) | 7B (FIG. 6B) |
| First reagent | | | | | | | | | |
| Surfactants (ppm) | Polyoxyethylene(15) oleyl ether | 12,500 | 7,500 | 10,500 | 6,000 | 20,000 | 6,000 | 20,000 | 2,000 |
| | Polyoxyethylene(20) oleyl ether | 12,500 | 7,500 | 24,500 | 14,000 | 30,000 | 9,000 | 30,000 | 3,000 |
| Sum of surfactants(ppm) | | 25,000 | 15,000 | 35,000 | 20,000 | 50,000 | 15,000 | 50,000 | 5,000 |
| Solubilizing agent (ppm) | Sodium N-lauroylsarcosinate | 1500 | 1500 | 750 | 750 | 750 | 750 | 250 | 250 |
| Buffering agent (mM) | HEPES | 30 | 30 | 30 | 30 | 30 | 30 | 30 | 30 |
| Saccharide (g/L) | Xylitol | 24.5 | 24.5 | — | — | — | — | — | — |
| Medium | Purified water | 1 L | 1 L | 1 L | 1 L | 1 L | 1 L | 1 L | 1 L |
| pH | | 7.0 | 7.0 | 7.0 | 7.0 | 7.0 | 7.0 | 7.0 | 7.0 |
| Second reagent | | | | | | | | | |
| Dye(ppm) | NK-321 | 50 | 50 | 50 | 50 | 50 | 50 | 50 | 50 |
| Medium | Ethylene glycol | 1 L | 1 L | 1 L | 1 L | 1 L | 1 L | 1 L | 1 L |

The first reagent (980 μL), 20 μL of the second reagent and 20 μl of a blood sample from a patient with leukemia were mixed and reacted at 35° C. for 13 seconds (7 seconds for Example 4) to prepare measurement samples. Scattergrams were obtained as described in Example 1. The same blood sample taken from the same patient was used as the sample for A and B in each Example. The different blood from different leukemia patients were used for respective Examples.

FIGS. 4 to 7 show the scattergrams obtained in Examples 4 to 7, respectively. In these Figures, (A) and (B) correspond to the results of the reagents A and B in each Example. In these scattergrams, the x-axis represents the side scattered light intensity and the y-axis represents the fluorescence intensity.

FIGS. 4 to 7 also show the ratio of myeloblasts to total leukocytes number ("BL region") calculated as described in Example 3. In each figure, the x-axis of the scattergram represents the side scattered light intensity and the y-axis represents the fluorescence intensity. According to the results of Examples 4 to 7, it is found that the myeloblast region could be identified without improper lysis of erythrocytes in the sample, even when the total concentration of the surfactants or the mixing ratio of two surfactants was varied in the reagent of the present invention.

The invention claimed is:

1. A method for analysis of myeloblasts, comprising:
preparing a measurement sample by mixing a peripheral blood sample and a reagent;
obtaining optical information including scattered light information and fluorescence information by applying light to blood cells in the measurement sample; and
distinguishing myeloblasts from other blood cells in the measurement sample based on the scattered light information and the fluorescence information, wherein the reagent comprises:
a surfactant which can damage cell membranes of erythrocytes and mature leukocytes,
a solubilizing agent which can shrink the damaged blood cells and a dye for staining nucleic acids represented by the following formula (I):

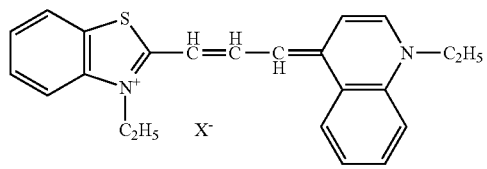
(I)

wherein X⁻ is an anion.

2. The method according to claim 1, wherein the step of distinguishing myeloblasts from other blood cells in the measurement sample based on the scattered light information and the fluorescence information comprises:
distinguishing leukocytes from other blood cells in the measurement based on the optical information; and
distinguishing the myeloblasts from leukocytes based on the scattered light information and the fluorescence information.

3. The method according to claim 1, wherein the scattered light information includes side scattered light information, and the step of distinguishing myeloblasts from other blood cells in the measurement sample based on the scattered light information and the fluorescence information distinguishes the myeloblasts from other blood cells in the measurement sample based on the side scattered light information and the fluorescence information.

4. The method according to claim 3, wherein
the scattered light information includes forward scattered light information, and the method comprises:
distinguishing myeloblasts from other blood cells in the measurement sample based on the forward scattered light information and the side scattered light information.

5. The method according to claim 3, wherein the scattered light information includes forward scattered light information, and the step of distinguishing myeloblasts from other blood cells in the measurement sample based on the scattered light information and the fluorescence information comprises:
distinguishing leukocytes from other blood cells in the measurement sample based on the forward scattered light information and the fluorescence information; and
distinguishing the myeloblasts from leukocytes based on the side scattered light information and the fluorescence information.

6. The method according to claim 5, comprising:
distinguishing myeloblasts from leukocytes based on the forward scattered light information and the side scattered light information.

7. The method according to claim 2, wherein the step of distinguishing the myeloblasts from leukocytes based on the scattered light information and the fluorescence information further comprises classifying the leukocytes as mature leukocytes and immature leucocytes.

8. The method according to claim 7, wherein the step of classifying the leukocytes as mature leukocytes and immature leucocytes further comprises classifying the mature leucocytes as lymphocytes, monocytes, and granulocytes.

9. The method according to claim 1, wherein
the step of obtaining optical information including scattered light information and fluorescence information by applying light to blood cells in the measurement sample comprises:
flowing the measurement sample through a flow cell;
applying light to the blood cells flowing through the flow cell; and
obtaining the optical information generated by the step of applying light to the blood cells flowing through the flow cell.

10. The method according to claim 1, wherein the surfactant is a nonionic surfactant.

11. The method according to claim 10, wherein the nonionic surfactant is a polyoxyethylene nonionic surfactant.

12. The method according to claim 11, wherein the polyoxyethylene nonionic surfactant has the following formula (III):

(III)

wherein R¹ represents a $C_{9-25}$ alkyl, alkenyl or alkynyl group; R² represents —O—, —COO— or

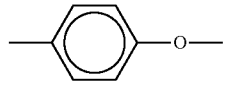

and n is an integer of 10 to 40.

13. The method according to claim 12, wherein the polyoxyethylene nonionic surfactant is polyoxyethylene oleyl ether or polyoxyethylene stearyl ether.

14. The method according to claim 13, wherein the polyoxyethylene oleyl ether has the formula (III) wherein n is 15 to 20.

15. The method according to claim 1, wherein the solubilizing agent is selected from the group consisting of a sarcosine derivative, a cholic acid derivative and methylglucanamide.

16. A method for analysis of myeloblasts, comprising:

preparing a measurement sample by mixing a peripheral blood sample, a first reagent, and a second reagent;

obtaining optical information including scattered light information and fluorescence information by applying light to blood cells in the measurement sample; and distinguishing myeloblasts from other blood cells in the measurement sample based on the scattered light information and the fluorescence information, wherein the first reagent comprises:

a surfactant which can damage cell membranes of erythrocytes and mature leukocytes and a solubilizing agent which can shrink the damaged blood cells, and the second reagent comprises:

a dye for staining nucleic acids represented by the following formula (I):

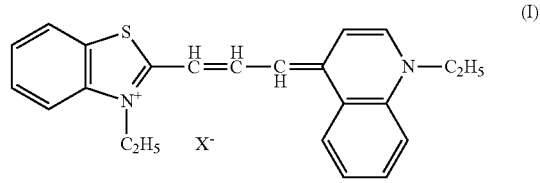

where X— is an anion.

17. The method according to claim 16, wherein the step of preparing a measurement sample by mixing a peripheral blood sample, a first reagent, and a second reagent comprises:

mixing the peripheral blood sample and the first reagent to obtain a mixture; and mixing the mixture and the second reagent.

18. The method according to claim 16, wherein the scattered light information includes side scattered light information, and the step of distinguishing myeloblasts from other blood cells in the measurement sample based on the scattered light information and the fluorescence information distinguishes the myeloblasts from other blood cells in the measurement sample based on the side scattered light information and the fluorescence information.

* * * * *